US008853428B2

United States Patent
Huet et al.

(10) Patent No.: US 8,853,428 B2
(45) Date of Patent: Oct. 7, 2014

(54) METHOD FOR PREPARING AN AMINO ACID FROM 2 AMINOBUTYROLACTONE

(75) Inventors: Robert Huet, Paris (FR); Jean-Michel Joerger, Villeurbanne (FR); Vivien Henryon, Lyons (FR)

(73) Assignee: Adisseo France S.A.S., Antony (FR)

( * ) Notice: Subject to any disclaimer, the term of this patent is extended or adjusted under 35 U.S.C. 154(b) by 6 days.

(21) Appl. No.: 13/821,318

(22) PCT Filed: Oct. 4, 2011

(86) PCT No.: PCT/FR2011/052302
§ 371 (c)(1),
(2), (4) Date: Mar. 7, 2013

(87) PCT Pub. No.: WO2012/045967
PCT Pub. Date: Apr. 12, 2012

(65) Prior Publication Data
US 2013/0184474 A1    Jul. 18, 2013

(30) Foreign Application Priority Data

Oct. 5, 2010    (FR) ..................... 10 58069

(51) Int. Cl.
*C07D 307/00* (2006.01)
(52) U.S. Cl.
USPC .......................................... 549/321
(58) Field of Classification Search
CPC ..................................... C07D 307/33
USPC .......................................... 549/321
See application file for complete search history.

(56) References Cited

U.S. PATENT DOCUMENTS

2008/0146840 A1    6/2008    Hateley et al.

FOREIGN PATENT DOCUMENTS

GB            651165 A    3/1951

*Primary Examiner* — Nizal Chandrakumar
(74) *Attorney, Agent, or Firm* — Porzio, Bromberg & Newman, P.C.

(57) ABSTRACT

The invention relates to a method for preparing an amino acid, or its salts, from 2-aminobutyrolactone (2ABL), said amino acid fitting the formula I, $XCH_2CH_2CHNH_2COOH$, wherein X is such that $X^-$ represents a nucleophilic ion, according to which N-carboxylation of 2-aminobutyrolactone (2ABL) is achieved with carbon dioxide, and the thereby obtained 2ABL carbamate is reactive with an XH reagent or its salts.

10 Claims, No Drawings

METHOD FOR PREPARING AN AMINO ACID FROM 2 AMINOBUTYROLACTONE

CROSS REFERENCE TO RELATED APPLICATION

This is a National Stage of International Application No. PCT/FR2011/052302, filed 4 Oct. 2011, which claims the benefit of application Ser. No. 10/58069, filed in France on 5 Oct. 2010, the disclosures of which Applications are incorporated by reference herein.

The present invention relates to a method for preparing an amino acid from 2-aminobutyrolactone (2ABL).

There exists a standard conversion of 2ABL into methionine by reaction of sodium methanethiolate ($CH_3SNa$), as described in Chem. Ber. (1950) 83, 265. This synthesis is carried out in a single step in toluene, at 160° C., over a duration of one hour. Its yield is however only 44%.

According to US2008/0146840A1, a method is known for obtaining methionine from homoserine, comprising the steps consisting of:
   a) carrying out a concomitant N-acylation and cyclization reaction of homoserine,
   b) reacting methylmercaptan with 2-aminobutyrolactone N-acetamide obtained in step a), in the presence of an acid or basic catalyst, in order to obtain methionine N-acetamide, and
   c) hydrolyzing methionine N-acetamide into methionine.

This method leads to higher yields, but it has the drawback of requiring three steps, each having to resort to purification of the intermediates formed.

Moreover, homoserine is a highly available compound. It may be obtained via a chemical route. It may also be obtained by microbiological fermentation of sugars; a wide bibliography exists on this subject. This source is all the more attractive since the isomer L of homoserine is obtained. As shown by the prior art, the step for cyclization of homoserine into 2ABL, either protected or not, is efficient but one is confronted with much too low yields of the ultimate methionine conversion step or with a highly burdensome method, in order to consider a large scale synthesis thereof.

The authors of the present invention have discovered a group protecting the amine function of 2ABL, as well as the reagent allowing its placement, said group being introduced and easily removed and this reversibly. Consequently, they have revealed a major application of homoserine in the preparation of amino acids.

The invention provides a method for preparing an amino acid, or one of its salts, from 2-aminobutyrolactone (2ABL), said amino acid fitting the formula I, $XCH_2CH_2CHNH_2COOH$, wherein X is such that $X^-$ represents a nucleophilic ion, which comprises the following steps:
   N-carboxylation of 2-aminobutyrolactone (2ABL) is achieved with carbon dioxide, and
   The N-carboxyl of the thereby obtained 2ABL is reacted with a reagent XH or its salts, and acidification is performed.

As the examples will illustrate this, the deprotection yields make an industrial synthesis of methionine possible from 2ABL. The industrial synthesis of many other amino acids, such as those fitting the formula I above may quite also be recommended. By amino acid, is meant any amino acid including an asymmetrical carbon bearing a group $-NH_2$, a group $-COOH$, $-H$ and a side chain of the form $-CH_2CH_2X$, X being provided according to the invention by the reagent XH or its salt, or of the form $-CH_2CH_2Y$, wherein Y represents a group resulting from conversion of X for example by hydrolysis. As preferred examples, mention may additionally be made of methionine, selenomethionine, homocysteine and glutamine. This method also allows preparation of homocysteine, the latter being obtained with its dimer.

As the carbon bearing the amino group and the carboxylic group is asymmetrical, by amino acid is meant any of its isomers, L- or D-, or their mixtures and notably the racemic mixture. The sought isomer or mixture of isomers of the amino acid are obtained from the corresponding isomer or mixture of isomers of 2ABL, and upstream from homoserine, the method subject matter of the invention not affecting the configuration of the entities.

Another object of the invention is N-carboxyl-2-aminobutyrolactone. This is an intermediate compound contained after the step for N-carboxylation of 2ABL. Of course, its application is not limited to this synthesis.

The N-carboxylation reaction is advantageously and simply achieved in the presence of bubbling of $CO_2$ gas. Preferably it is conducted in an aprotic polar solvent. As an example, the latter is selected from dimethylsulfoxide and N-methylpyrrolidone (NMP). It may also be conducted with supercritical $CO_2$.

This step is preferably conducted at a temperature comprised between 0 and 50° C.

The second step of the method sets into play a reagent XH or a salt of the latter. X is defined such that $X^-$ is an ion, consisting of one or several atoms, which is nucleophilic. More specifically, it is capable of acting on the beta carbon of the protected amine function, in order to open the lactone ring. It comprises an atom rich in electrons generally selected from sulfur, selenium, oxygen, carbon atoms, said atom then being bound to at least one of a hydrogen, a linear or branched C1-C6 alkyl, a nitrogen. As examples, $X^-$ is selected from $CH_3S^-$ and $CH_3Se^-$ for obtaining methionine and selenomethionine, respectively from $SH^-$ and $SeH^-$ for obtaining homocysteine and 2-amino-4-SeH-thiobutyric acid, respectively. It may also be $CN^-$ for obtaining 2-amino-4-cyanothiobutyric acid; the latter will advantageously be hydrolyzed into an amide group in order to lead to glutamine.

The XH salts are advantageously selected from metal salts, for example alkaline and earth alkaline metals.

The concentration of the XH reagent or its salt is advantageously in excess relatively to 2-ABL, it preferably represents 3 to 30% in a weight/weight percentage of the total mass of the reaction medium. This step preferably takes place at a temperature varying from 100 to 200° C. Advantageously, the temperature is of the order of 130° C.

The method of the invention may be applied over a period varying from 5 minutes to 3 hours.

As indicated earlier, with this method it is possible to obtain an amino acid or its salts. Its salts are advantageously selected from sodium, lithium, calcium, zinc salts. In order to obtain a salt, the suitable salt of the XH reagent will be selected.

The invention and advantages thereof are illustrated hereafter with the support of the following examples describing the preparation of methionine according to Examples 1 and 2, of homocysteine and its dimer according to Example 3, and of selenomethionine according to Examples 4, 5, 6 and 7, from 2ABL.

Examples 1 and 2 describe the preparation of methionine directly from 2ABL (example 1) and from 2ABL while passing through the N-carboxylated-2ABL intermediate, i.e. according to the invention (Example 2), according to the following scheme:

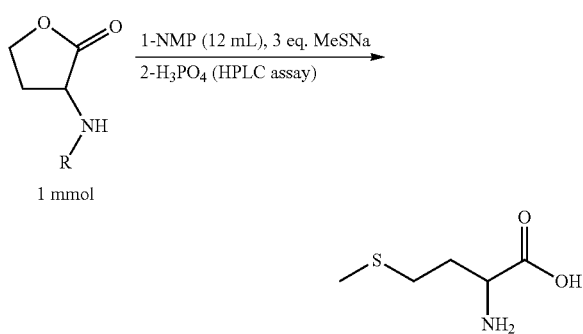

R=H : 2ABL MTN
R=COOH : 2-ABL-N-carbonate

EXAMPLE 1

Preparation of Methionine Directly from 2ABL

This test is conducted at the scale of 1 mmol of 2-ABL. 2-ABL is placed in solution in 1.2 mL of NMP. Stirring is maintained at 20° C. for 10 mins, and then 10.8 mL of NMP and 3 eq. of MeSNa are added. The reaction medium placed under stirring is heated to 150° C. for 1 hour. The medium is hydrolyzed by simple dilution in the HPLC solvent.

EXAMPLE 2

Preparation of Methionine According to the Invention

The reaction scheme is the following:

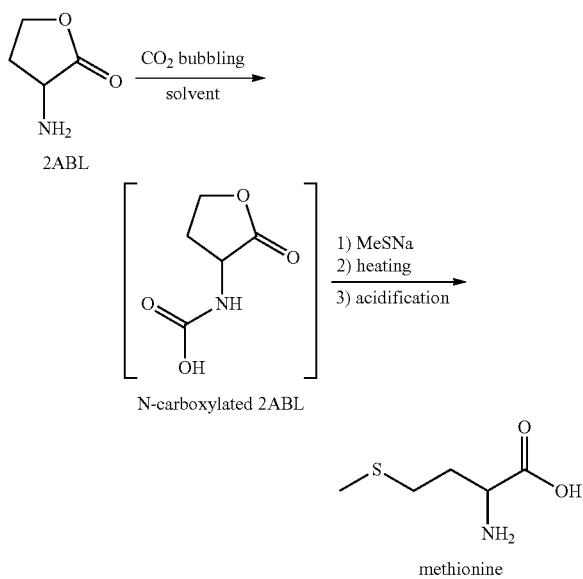

The operating conditions of Example 1 are reproduced identically, with the only difference that $CO_2$ bubbling is performed at 20° C. for 10 min.

The obtained results are presented in the following Table 1:

| | | % Yield (HPLC) | | |
|---|---|---|---|---|
| Example | Substrate | Methionine | Diketopiperazine | Homoserine |
| 1 | 2ABL | 17 | 19 | 29 |
| 2 | N-carboxylated 2ABL | 80 | 16 | <1 |

A four-fold increase in the methionine yield as prepared by the method of the invention is observed.

Example 3 describes the preparation of homocysteine from 2ABL according to the invention.

EXAMPLE 3

Preparation of Homocysteine According to the Invention

The reaction scheme is the following:

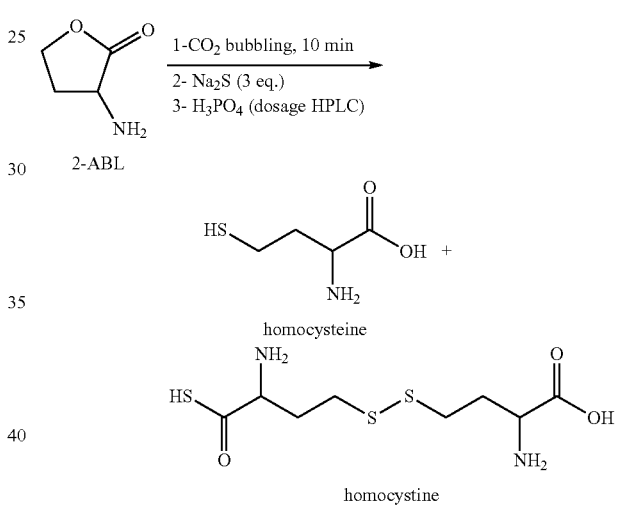

With the method of the invention, it is also possible to obtain the dimer of homocysteine (called homocystine).

This example is carried out on a scale of 1 mmol of 2ABL in a pill box with magnetic stirring. The 2-ABL is placed in solution in 1.2 mL of NMP. $CO_2$ bubbling is carried out at 20° C. for 10 mins, and then 10.8 mL of NMP and 3 equivalents of $Na_2S$ are added. The reaction medium placed under stirring is gradually heated up to 90° C. After 30 mins, the medium is hydrolyzed by simple dilution in the HPLC solvent.

These conditions allow formation of homocysteine and of its dimer. The best performances are obtained at a temperature of 90° C.

After a reaction time of 30 mins, the reaction is completed. At a higher temperature and in the presence of 3 equivalents of $Na_2S$, homocystine is favored. Excess $Na_2S$ accelerates dimerization of homocysteine.

The following yields (HPLC) are obtained:

| | |
|---|---|
| Homocysteine | 36% |
| Homocystine | 14% |
| Diketopiperazine | 2% |

Examples 4, 5, 6 and 7 describe the preparation of selenomethionine directly from 2ABL (Examples 4 and 6) and from 2ABL via the N-carboxylated 2ABL intermediate, i.e. according to the invention (Examples 5 and 7) by reaction with MeSeNa or MeSeLi.

According to Examples 4 and 5, the scheme is the following:

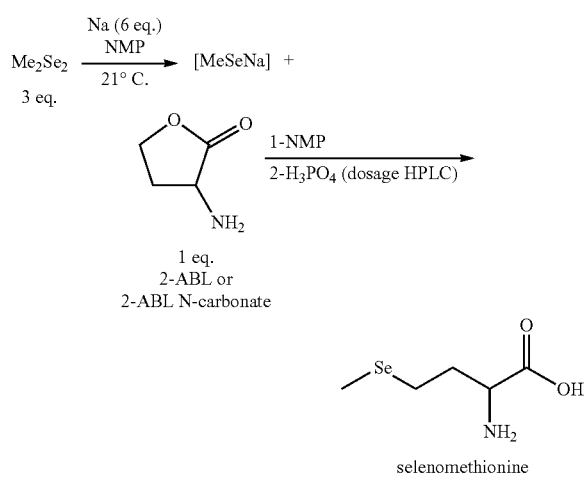

According to Examples 6 and 7, the scheme is the following:

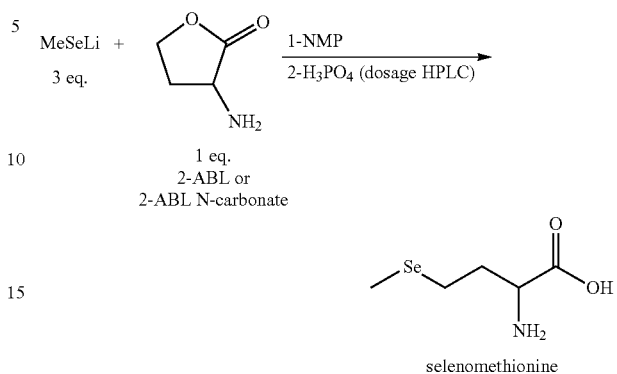

MeSeLi is prepared according to the synthesis described in M. Tiecco et al., Synthetic Communications, 1983, 13, 617.

EXAMPLE 4

Preparation of Selenomethionine Directly from 2ABL

This example is carried out on a scale of 50 mg of Na, in a pill box of 4 mL with magnetic stirring at 20° C. The $Me_2Se_2$ is placed in solution in 2 mL of NMP and then at 20° C., 50 mg of Na are added. The 2-ABL is placed in solution in 870 μL of NMP. Stirring is maintained at 20° C. for 10 mins, and then 10.8 mL of NMP and the solution of MeSeNa in NMP are added. The reaction medium placed under stirring is heated to 90° C. for 1 hour. The reaction medium is hydrolyzed by simple dilution in the HPLC solvent.

EXAMPLE 5

Preparation of Selenomethionine According to the Invention

The operating conditions of Example 4 are reproduced identically with the only difference that $CO_2$ bubbling is performed.

The obtained results are presented in the following table 2:

| | | % Yield (HPLC) | |
|---|---|---|---|
| Example | Substrate | Selenomethionine | Diketopiperazine |
| 4 | 2ABL | 17 | 2 |
| 5 | N-carboxylated 2ABL | 51 | 2 |

EXAMPLE 6

Preparation of Methionine Directly from 2ABL

This example is carried out on a scale of 1 mmol of 2ABL in a pill box with magnetic stirring at 20° C. The 2-ABL is placed in solution in 1.2 mL of NMP. Stirring is maintained at 20° C. for 10 mins, and then 10.8 mL of NMP et 2.43 mL of MeSeLi in solution in THF are added. The reaction medium placed under stirring is heated for 1 hour at 60° C. The reaction medium is hydrolyzed by simple dilution in the HPLC solvent.

EXAMPLE 7

Preparation de Selenomethionine According to the Invention

The operating conditions of Example 6 are reproduced identically, with the only approximate differences that $CO_2$ bubbling is carried out at 20° C. for 10 mins and that the reaction temperature is raised to 90° C.

The obtained results are presented in the following Table 3:

| | | Temperature | % Yield (HPLC) | |
|---|---|---|---|---|
| Example | Substrate | (° C.) | Selenomethionine | Diketopiperazine |
| 6 | 2ABL | 60 | 60 | 5 |
| 7 | N-carboxylated 2ABL | 90 | 92 | 5 |

From the whole of these examples, it emerges that the method is a highly performing route for obtaining amino acids from 2ABL and is in that a novel interesting exploitation of homoserine.

The intermediate compound N-carboxyl-2-aminobutyrolactone, one of the objects of the invention notably formed in Examples 2, 3, 5 and 7 was analyzed. These analysis are the following:

Proton NMR spectrum (frequency: 250 MHz, solvent dmso-d6): 2.16 ppm (multiplet, 1H), 2.28-2.44; (multiplet, 1H), 4.08-4.22; (multiplet, 1H), 4.23-4.38; (multiplet, 2H), 7.25; (doublet, J=8.2 Hz, 1H)

The invention claimed is:

1. A method for preparing an amino acid, or its salts, from 2-aminobutyrolactone (2ABL), said amino acid fitting the formula I, $XCH_2CH_2CHNH_2COOH$, wherein X is such that $X^-$ represents a nucleophilic ion, characterized in that it comprises the following steps:

N-carboxylation of 2-aminobutyrolactone (2ABL) is achieved with carbon dioxide, and the thereby obtained N-carboxylated 2ABL is reacted with a reagent XH or its salts and acidification is performed.

2. The method according to claim 1, characterized in that $X^-$ is selected from $CH_3S^-$, $CH_3Se^-$, $SH^-$, $SeH^-$, $CN^-$.

3. The method according to claim 1, characterized in that an amino acid selected from methionine and selenomethionine.

4. The method according to claim 1, characterized in that homocysteine and its dimer are obtained.

5. The method according to claim 1, characterized in that N-carboxylation is carried out in an aprotic polar solvent.

6. The method according to claim 5, characterized in that the solvent is selected from dimethylsulfoxide and N-methylpyrrolidone.

7. The method according to claim 1, characterized in that the L isomer of the amino acid, the D isomer or mixtures of the latter and notably the racemic mixture are prepared from the corresponding form of 2ABL.

8. The method according to claim 1, characterized in that 2ABL is obtained from homoserine.

9. The method according to claim 8, characterized in that homoserine is the L isomer and is obtained by microbiological fermentation of sugars of natural origin.

10. The method according to claim 1, characterized in that the salts of the amino acid are selected from sodium, lithium, calcium, zinc salts.

* * * * *